(12) United States Patent
Morris et al.

(10) Patent No.: US 11,782,282 B1
(45) Date of Patent: Oct. 10, 2023

(54) FACIAL INTERFACE ASSEMBLIES FOR HEAD-MOUNTED DISPLAYS AND RELATED SYSTEMS AND METHODS

(71) Applicant: Meta Platforms, Inc., Menlo Park, CA (US)

(72) Inventors: Quintin Morris, Seattle, WA (US); Shane Michael Ellis, Bellevue, WA (US); Scott Andrew Dallmeyer, Seattle, WA (US); Peter Wesley Bristol, Seattle, WA (US); David Michael Pickett, Seattle, WA (US); Joel Bernard Jacobs, Seattle, WA (US); Yi-Yaun Chen, Seattle, WA (US); Enric Vial Roig, Seattle, WA (US)

(73) Assignee: Meta Platforms, Inc., Menlo Park, CA (US)

( * ) Notice: Subject to any disclaimer, the term of this patent is extended or adjusted under 35 U.S.C. 154(b) by 0 days.

(21) Appl. No.: 18/048,775

(22) Filed: Oct. 21, 2022

Related U.S. Application Data

(63) Continuation of application No. 16/213,544, filed on Dec. 7, 2018, now Pat. No. 11,480,801.

(51) Int. Cl.
*G02B 27/01* (2006.01)
*F16M 13/02* (2006.01)
*A61F 9/02* (2006.01)

(52) U.S. Cl.
CPC ............ *G02B 27/0176* (2013.01); *A61F 9/02* (2013.01); *F16M 13/02* (2013.01)

(58) Field of Classification Search
CPC ........ G02B 27/0176; A61F 9/02; F16M 13/02
See application file for complete search history.

(56) References Cited

U.S. PATENT DOCUMENTS

| | | | |
|---|---|---|---|
| 6,369,952 B1 | 4/2002 | Rallison et al. | |
| 2004/0057138 A1* | 3/2004 | Tanijiri | G02B 27/0172 359/868 |
| 2004/0143889 A1* | 7/2004 | Chou | A63B 33/004 2/445 |
| 2006/0143766 A1 | 7/2006 | Ramsey | |
| 2012/0255104 A1* | 10/2012 | Didier | A61F 9/025 2/426 |
| 2014/0157496 A1* | 6/2014 | Ginther | A61F 9/02 2/439 |
| 2015/0234189 A1* | 8/2015 | Lyons | G02B 27/017 345/174 |

(Continued)

*Primary Examiner* — Mark Edwards
(74) *Attorney, Agent, or Firm* — Greenberg Traurig, LLP

(57) ABSTRACT

The disclosed flexible facial interface assemblies for head-mounted display systems may include a rigid support frame element and a flexible facial interface frame element. The rigid support frame element may be shaped and configured to physically support a display of a head-mounted display system in front of a user's eyes when the facial interface assembly is worn by the user. The flexible facial interface frame element may be configured to flex to conform to the user's facial features when the facial interface assembly is worn by the user. An outer periphery of the flexible facial interface frame element may be independently movable relative to an outer periphery of the rigid support frame element. Various other systems and methods are also disclosed.

20 Claims, 9 Drawing Sheets

(56) References Cited

U.S. PATENT DOCUMENTS

| | | | |
|---|---|---|---|
| 2015/0316773 A1* | 11/2015 | Tazbaz | G02B 27/0179 359/630 |
| 2016/0353062 A1 | 12/2016 | Ono et al. | |
| 2017/0094816 A1 | 3/2017 | Yun et al. | |
| 2017/0153672 A1 | 6/2017 | Shin et al. | |
| 2017/0318281 A1 | 11/2017 | Edlund et al. | |
| 2019/0258065 A1 | 8/2019 | Yun et al. | |

* cited by examiner

FACIAL INTERFACE ASSEMBLIES FOR HEAD-MOUNTED DISPLAYS AND RELATED SYSTEMS AND METHODS

CROSS REFERENCE TO RELATED APPLICATION

This application is a continuation of U.S. application Ser. No. 16/213,544, filed 7 Dec. 2018, the disclosure of which is incorporated, in its entirety, by this reference.

BACKGROUND

Head-mounted display systems include a display element positioned directly in front of a user's eyes. Artificial reality ("AR") systems (e.g., virtual reality, augmented reality, mixed reality, or hybrid reality systems) often employ head-mounted displays to present images of virtual objects or scenes to the user. The virtual objects or scenes may be part of an entirely virtual environment viewed by the user or may overlay views of a real-world environment surrounding the user.

When worn by the user, head-mounted displays are conventionally supported on the user's head in a variety of ways. For example, a halo-type head-mounted display may include a head strap that extends from the user's forehead and wraps circumferentially around the user's head. A harness-type head-mounted display may include one or more straps or supports that extend over a top of the user's head for additional support.

At least a portion of the weight of the displays and other elements of the head-mounted displays is held in front of the user's face. This weight may cause discomfort on the user's head, face, and nose particularly after elongated periods of use. Thus, foam or other conformable features are included on some head-mounted displays in an attempt to improve user comfort. However, different users have faces and heads with features in a wide variety of sizes and shapes, which makes it difficult to achieve user comfort for a range of users. Additionally, the displays and other elements are conventionally rigid and non-conformable to the user's facial features.

SUMMARY

As will be described in greater detail below, the present disclosure describes facial interface assemblies, systems, and related methods, such as for head-mounted display systems, that may include a rigid support frame element to physically support a display and a flexible facial interface frame element to conform to the user's facial features.

In some embodiments, the present disclosure includes facial interface assemblies for a head-mounted display system. Such facial interface assemblies may include a rigid support frame element dimensioned to physically support a display of a head-mounted display system in front of a user's eyes when the facial interface assembly is worn by the user. The facial interface assemblies may also include a flexible facial interface element configured to flex to conform to the user's facial features when the facial interface assembly is worn by the user. An outer periphery of the flexible facial interface frame element may be independently movable relative to an outer periphery of the rigid support frame element.

In some examples, the facial interface assemblies may also include an extensible material disposed between the rigid support frame element and the flexible facial interface frame element. The extensible material may be configured to extend upon flexing of the flexible facial interface frame element away from the rigid support frame element and to retract upon flexing of the flexible facial interface frame element toward the rigid support frame element. The extensible material may include a flexible fabric material, such as at least one of a woven fabric material, a non-woven fabric material, a fabric material that is at least partially transmissive to visible light, or a fabric material that is opaque to visible light. The extensible material may include a flexible foam material, such as at least one of a closed cell foam material or an open cell foam material.

In additional examples, the rigid support frame element may be coupled to the flexible facial interface frame element with at least one central support element. The at least one central support element may include an upper central support element coupling an upper portion of the rigid support frame element to an upper portion of the flexible facial interface frame element. The upper central support element may be positioned to be over the user's nose when the facial interface assembly is worn by the user. The at least one central support element may also include at least one lower central support element coupling a lower portion of the rigid support frame element to a lower portion of the flexible facial interface frame element. The at least one lower central support element may include a single lower central support element positioned to be over the user's nose when the facial interface assembly is worn by the user. In some examples, the at least one lower central support element may include a first lower central support element to be positioned under the user's first eye and a second lower central support element positioned to be over the user's second eye when the facial interface assembly is worn by the user. The flexible facial interface frame element may include a nasal bridge portion that is configured to flex inward or outward to accommodate a shape of the user's nasal bridge when the facial interface assembly is worn by the user.

In further examples, the rigid support frame element and the flexible facial interface frame element may include a same material. The rigid support frame element and the flexible facial interface frame element may be parts of a unitary, integral frame body. A head strap may extend from the outer periphery of the flexible facial interface frame element. The head strap may include a same material as the flexible facial interface frame element. The flexible facial interface frame element may include a flexible flange that includes slits to increase a flexibility of the flexible facial interface frame element.

In some embodiments, the present disclosure may include head-mounted display systems. Such head-mounted display systems may include a display configured to display images to a user's eyes when the head-mounted display system is worn by the user, and a facial interface assembly. The facial interface assembly may include a rigid support frame element that may be configured to physically support the display in front of the user's eyes when the facial interface assembly is worn by the user. The facial interface assembly may also include a flexible facial interface frame element that is configured to flex to conform to the user's facial features when the facial interface assembly is worn by the user. An outer periphery of the flexible facial interface frame element may be independently movable relative to an outer periphery of the rigid support frame element.

In some examples, the display may be removable and replaceable relative to the facial interface assembly. The facial interface assembly may also include an extensible material disposed between the rigid support frame element and the flexible facial interface frame element and configured to extend upon flexing of the flexible facial interface frame element away from the rigid support frame element.

In some embodiments, the present disclosure includes methods of forming a facial interface assembly for a head-mounted display system. In accordance with such methods, a rigid support frame element may be coupled to a flexible facial interface frame element. The rigid support frame element may be configured to physically support a display of a head-mounted display system. The flexible facial interface frame element may be configured to form to a user's facial features when the facial interface assembly is worn by the user. an outer periphery of the flexible facial interface frame element is independently movable relative to an outer periphery of the rigid support frame element. An extensible material may be disposed between the rigid support frame element and the flexible facial interface frame element. The extensible material may be configured to extend upon flexing of the flexible facial interface frame element away from the rigid support frame element and to retract upon flexing of the flexible facial interface frame element toward the rigid support frame element.

Features from any of the embodiments described herein may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of example embodiments and are a part of the specification. Together with the following description, these drawings demonstrate and explain various principles of the instant disclosure.

Figure 1:
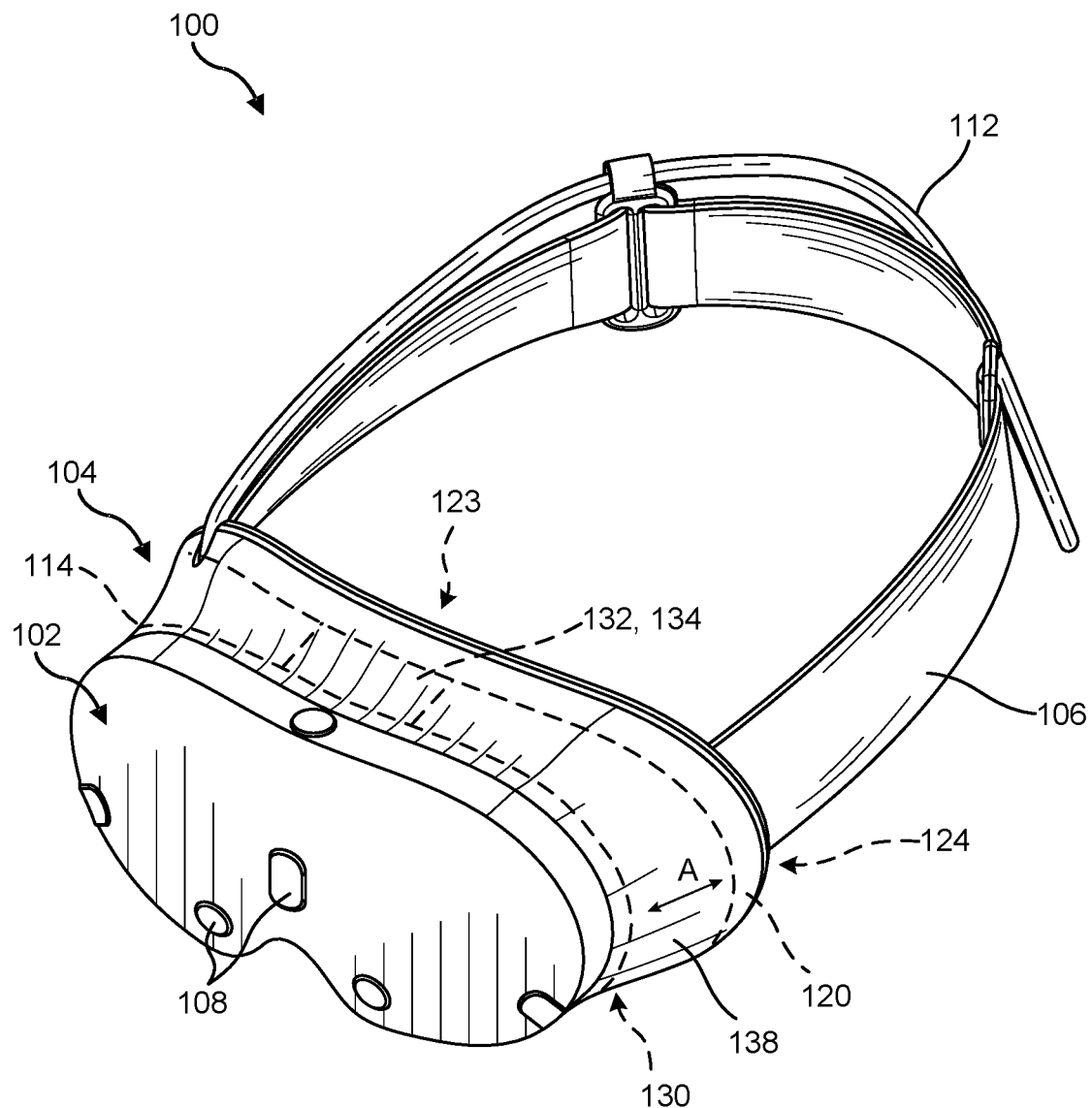
FIG. 1 is a top front perspective view of a head-mounted display system, according to at least one embodiment of the present disclosure.

Throughout the drawings, identical reference characters and descriptions indicate similar, but not necessarily identical, elements. While the example embodiments described herein are susceptible to various modifications and alternative forms, specific embodiments have been shown by way of example in the drawings and will be described in detail herein. However, the example embodiments described herein are not intended to be limited to the particular forms disclosed. Rather, the instant disclosure covers all modifications, equivalents, and alternatives falling within the scope of the appended claims.

DETAILED DESCRIPTION OF EXAMPLE EMBODIMENTS

The present disclosure is generally directed to facial interface assemblies and related systems and methods, such as for head-mounted displays (e.g., artificial reality displays). As will be explained in greater detail below, embodiments of the instant disclosure may relate to facial interface assemblies that include a rigid support frame element and a flexible facial interface frame element. The flexible facial interface frame element may include an outer periphery that is independently movable relative to an outer periphery of the rigid support frame element. In some examples, an extensible material may be disposed between the flexible facial interface frame element and the rigid support frame element. Such facial interface assemblies may enable a comfortable and adaptable fit for a variety of different face shapes and sizes.

The following will provide, with reference to FIGS. 1-9, detailed descriptions of various embodiments of facial interface assemblies for head-mounted display systems. Detailed descriptions of example methods of forming facial interface assemblies are provided with reference to FIG. 10.

Figure 2:
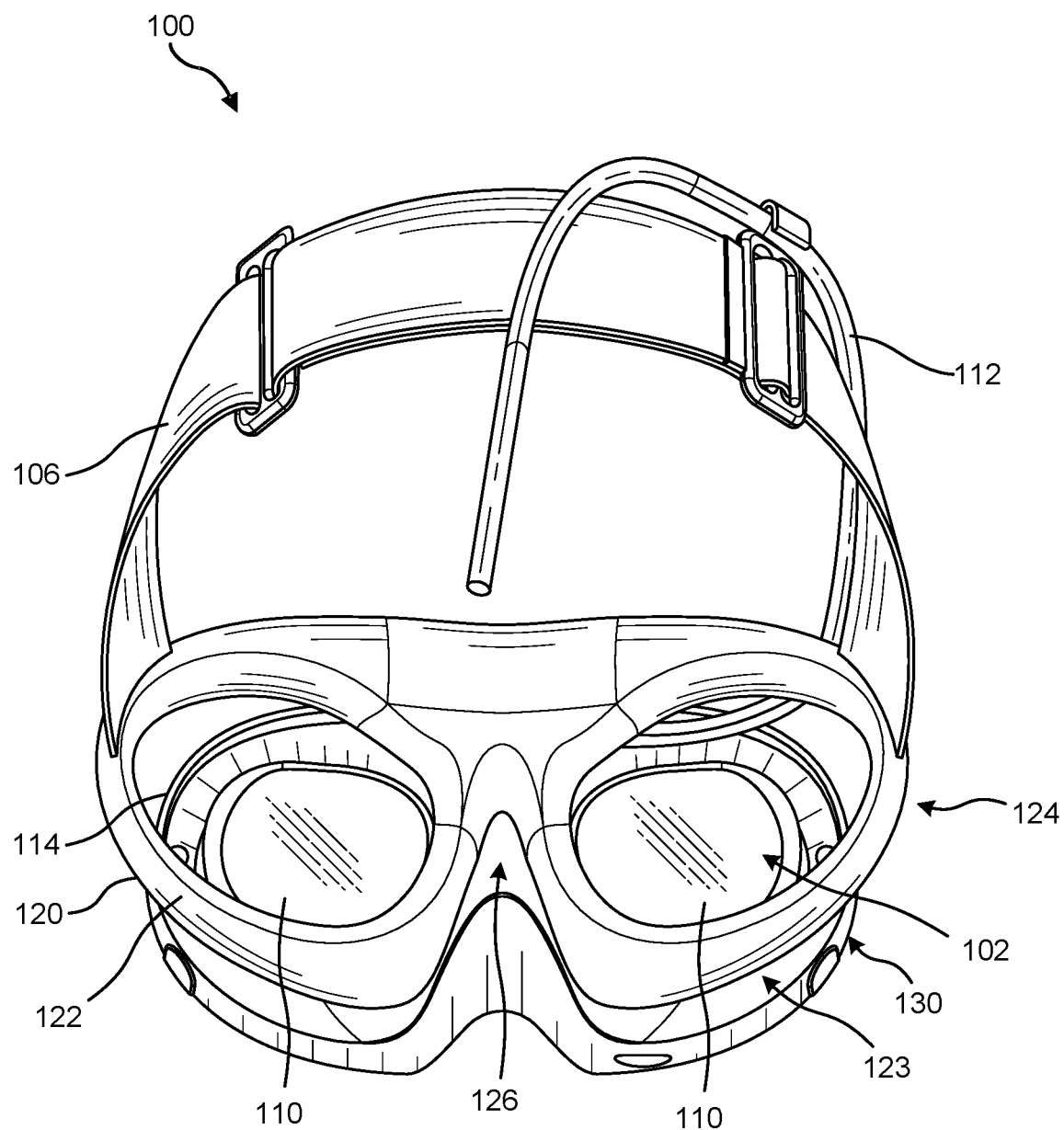
FIG. 2 is a bottom back perspective view of the head-mounted display system of FIG. 1.
Figure 3:
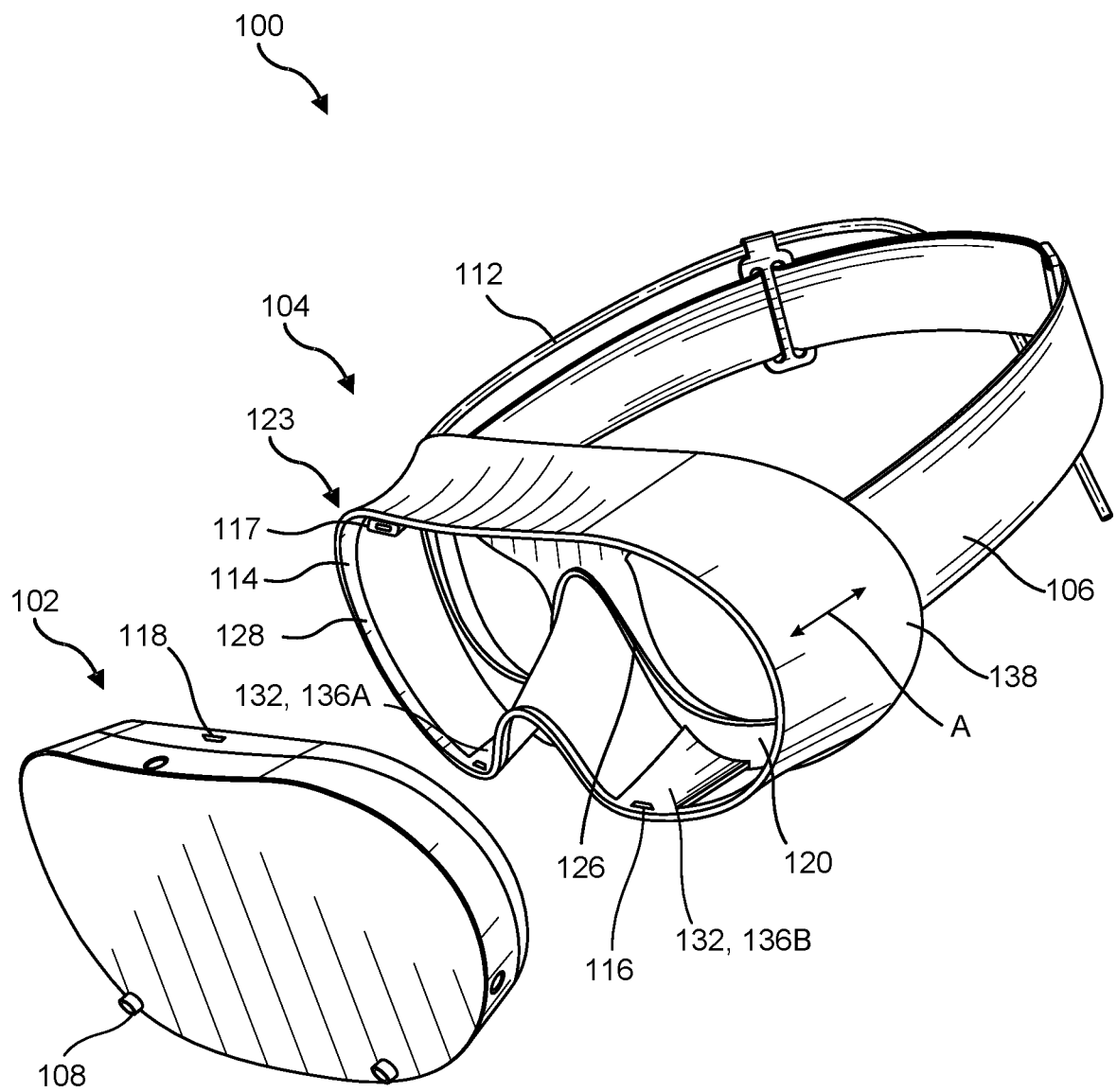
FIG. 3 is a perspective view of the head-mounted display system of FIGS. 1 and 2 in a partially disassembled state, according to at least one embodiment of the present disclosure.

FIG. 1 is a top front perspective view of a head-mounted display ("HMD") system 100. FIG. 2 is a bottom back perspective view of the HMD system 100. FIG. 3 is a perspective view of the HMD system 100 in a partially disassembled state. Referring to FIGS. 1-3, the HMD system 100 may include a display 102, a facial interface assembly 104 for supporting the display 102 and for resting the HMD system 100 against a user's face, and a head strap 106 for securing the HMD system 100 on the user's head.

The display 102 may include an electronic display for an artificial reality (e.g., virtual reality, augmented reality, mixed reality, hybrid reality, etc.) system, for example. The display 102 may include one or more display elements (e.g., LCD display elements, image combiners, hot mirrors, LED displays, OLED displays, etc.), a graphics processing unit for rendering an image on the display element, one or more image sensors 108 (e.g., cameras), one or more optical lenses 110, an eye-tracking element, a GPS sensor, one or more motion sensors (e.g., accelerometers, proximity sensors, light sources (e.g., infrared light sources), a power source, a wireless or wired communication component, etc. The power source and/or wired communication component, if present, may include an electrical cable 112, which may extend from the display 102 to a computer, controller, battery pack, electrical outlet, mobile device, etc.

In some embodiments, the display 102 may be removable and replaceable relative to the facial interface assembly 104, as shown in FIG. 3. For example, the facial interface assembly 104 may be configured to interchangeably support different displays 102, or to remove and replace the display 102 for cleaning the display 102 and/or the facial interface assembly 104, for electrically charging the display 102, or for other maintenance to the display 102.

The facial interface assembly 104 may include a rigid support frame element 114 that is shaped and configured to physically support the display 102 in front of a user's eyes when the facial interface assembly 104 is worn by the user. Thus, the shape of the rigid support frame element 114 may be complementary to a shape of the display 102. The rigid support frame element 114 may include one or more display engagement elements 116 (shown in FIG. 3), such as magnets, notches, bumps, latches, clips, etc. for removably coupling the display 102 to the rigid support frame element 114. In some examples, an electrical connector 117 (FIG. 3) may be disposed on the rigid support frame element 114, such as to connect the display 102 to the electrical cable 112. Corresponding frame engagement elements 118 and/or a corresponding electrical connector may be included in the display 102. In additional embodiments, the display 102 may be removably coupled to the rigid support frame element 114 without use of the engagement elements 116, 118. For example, the display 102 may snugly fit within the rigid support frame element 114 and may be held in place by friction.

The facial interface assembly 104 may also include a flexible facial interface frame element 120 that is configured to flex to conform to the user's facial features when the HMD system 100 is worn by the user. A facial interface padding 122 (shown in FIG. 2) may be disposed on an inner (i.e., toward the user's face when worn) surface of the flexible facial interface frame element 120 to provide a comfortable fit against the user's face. The facial interface padding 122 may include, for example, a closed cell foam or an open cell foam, which may or may not be covered by a fabric material. A frame body 123 of the facial interface assembly 104 may include both the rigid support frame element 114 and the flexible facial interface frame element 120.

At least a portion (e.g., an outer periphery 124, a nasal bridge portion 126, etc.) of the flexible facial interface frame element 120 may be flexible in a forward and backward direction A (relative to a user wearing the HMD system 100) to flex and conform to the user's facial size and shape when the HMD system 100 is worn by the user. In some examples, the terms "flexible" and "rigid" may be used in a relative sense. For example, the flexible facial interface frame element 120 may be relatively more flexible than the rigid support frame element 114 in the forward and backward direction A, even though both of these elements may exhibit some level of flexibility. For example, both of the flexible facial interface frame element 120 and the rigid support frame element 114 may be formed of the same material. By way of example and not limitation, the flexible facial interface frame element 120 and the rigid support frame element 114 may be formed of a polymer material, a metal material, a fiber-matrix composite material, or a combination thereof. In one non-limiting example, the frame body 123, including the flexible facial interface frame element 120 and the rigid support frame element 114, may be formed of a thermoplastic polymer material, such as nylon.

The relative flexibility of the flexible facial interface frame element 120 may be accomplished by the material properties and/or configuration of the material forming the flexible facial interface frame element 120. For example, a thickness of the flexible facial interface frame element 120 in the forward and backward direction A (relative to a user wearing the HMD system 100) may be sufficiently small to enable flexing in the forward and backward direction A with an application of a relatively small force (e.g., a force applied by the head strap 106 to comfortably hold the HMD system 100 on the user's head). Due to its flexibility in at least the forward and backward direction A, the flexible facial interface frame element 120 may be customizable and adaptable to a variety of different face shapes, features, and/or sizes, as will be explained further below with reference to FIGS. 5A and 5B. In additional examples, the material of the flexible facial interface frame element 120 may be selected for its flexibility. For example, the flexible facial interface frame element 120 may be or include a foam material, which may or may not be covered with a flexible coating, such as a silicone or rubber coating.

The relative rigidity of the rigid support frame element 114 may be accomplished by the material properties and/or configuration of the material forming the rigid support frame element 114. For example, the rigid support frame element 114 may be or include a lip 128 having a width in a generally forward and backward direction A (relative to a user wearing the HMD system 100) that is sufficient to reduce flexibility of at least a portion (e.g., an outer periphery 130) of the rigid support frame element 114 in the forward and backward direction A. In addition, coupling the display 102 to the rigid support frame element 114 may further inhibit flexing of the rigid support frame element 114 in the forward and backward direction A.

The rigid support frame element 114 may be coupled to (e.g., attached to, adhered to, integrally formed with, or fastened to, etc.) and physically supported by the flexible facial interface frame element 120. At least one central support element 132 may couple the rigid support frame element 114 to the flexible facial interface frame element 120. The at least one central support element 132 may include, for example, an upper central support element 134 extending between and coupling an upper portion of the rigid support frame element 114 to an upper portion of the flexible facial interface frame element 120. The upper central support element 134 may be positioned to be over the user's nose when the HMD system 100 is worn by the user. The upper central support element 134 may be sized and configured to physically support at least a portion of the rigid support frame element 114 and the display 102. The upper central support element 134 may also provide a standoff between the rigid support frame element 114 and the flexible facial interface frame element 120, such as to provide space for components of the display 102, to provide relief for the user's nose, etc.

The at least one central support element 132 may also include at least one lower central support element 136 coupling a lower portion of the rigid support frame element 114 to a lower portion of the flexible facial interface frame element 120. For example, the at least one lower central support element 136 may include a first lower central support element 136A positioned to be under the user's first eye and a second lower central support element 136B positioned to be under the user's second eye when the HMD system 100 is worn by the user.

The frame body 123 may include and/or be defined by the rigid support frame element 114, the flexible facial interface frame element 120, and the at least one central support element 132 (e.g., the upper central support element 134 and the first and second lower central support elements 136A, 136B). In some embodiments, these components of the frame body 123 may be parts of an integral, unitary frame body 123. For example, the rigid support frame element 114, the flexible facial interface frame element 120, and the at least one central support element 132 may be formed by a molding and/or three-dimensional printing process. In additional embodiments, the components of the frame body 123 may be formed separately from each other and secured together, such as via fasteners, welds, and/or adhesives.

In some examples, the at least one central support element 132 may have a variable and controllable length. For example, a user may be able to modify a distance between the user's eyes and the display 102 or an angle of the display 102 relative to the user's eyes by turning a screw or actuating a linear actuator to modify a length of the at least one central support element 132 (e.g., by modifying a length of one or more of the upper central support element 134, the first lower central support element 136A, or the second lower central support element 136B).

The frame body 123 of the facial interface assembly 104 may lack any support element between the outer periphery 124 of the flexible facial interface frame element 120 and the outer periphery 130 of the rigid support frame element 114. Thus, the outer periphery 124 of the flexible facial interface frame element 120 may be independently movable (e.g., in the forward and backward direction A relative to the user wearing the HMD system 100) relative to the outer periphery 130 of the rigid support frame element 114. Therefore, flexing of at least the outer periphery 124 of the flexible facial interface frame element 120 to conform to the user's facial features upon wearing the HMD system 100 may be substantially unimpeded by the rigid support frame element 114 and the display 102.

In some examples, the term "substantially" in reference to a given parameter, property, or condition may refer to a degree that one skilled in the art would understand that the given parameter, property, or condition is met with a small degree of variance, such as within acceptable manufacturing tolerances. For example, a parameter that is substantially met may be at least about 90% met, at least about 95% met, or at least about 99% met.

In some embodiments, the facial interface assembly 104 of the HMD system 100 may include an extensible material 138 disposed between the rigid support frame element 114 and the flexible facial interface frame element 120. The extensible material 138 may be configured to extend upon flexing of the flexible facial interface frame element 120 away from the rigid support frame element 114 and to retract upon flexing of the flexible facial interface frame element 120 toward the rigid support frame element 114. For example, the extensible material 138 may be or include a flexible fabric material, such as one or more of a woven fabric material, a non-woven fabric material, a fabric material that is at least partially transmissive to visible light, or a fabric material that is opaque to visible light. In additional examples, the extensible material 138 may be or include a flexible foam material, such as at least one of a closed cell foam material or an open cell foam material. The extensible material 138 may exhibit material properties that facilitate extension and/or retraction without substantially inhibiting flexing of the flexible facial interface frame element 120 away from the rigid support frame element 114 to conform to the user's facial features.

The extensible material 138 may, in some embodiments, be configured to block visible light from entering into the HMD system 100 when worn by the user. The extensible material 138 may also be configured to inhibit passage of debris (e.g., dust) into an interior of the HMD system 100 when worn. In some embodiments, the extensible material 138 may be or include a breathable fabric material to enable cooling of the interior of the HMD system 100 and/or to inhibit condensation of perspiration within the interior of the HMD system 100.

Figure 4:
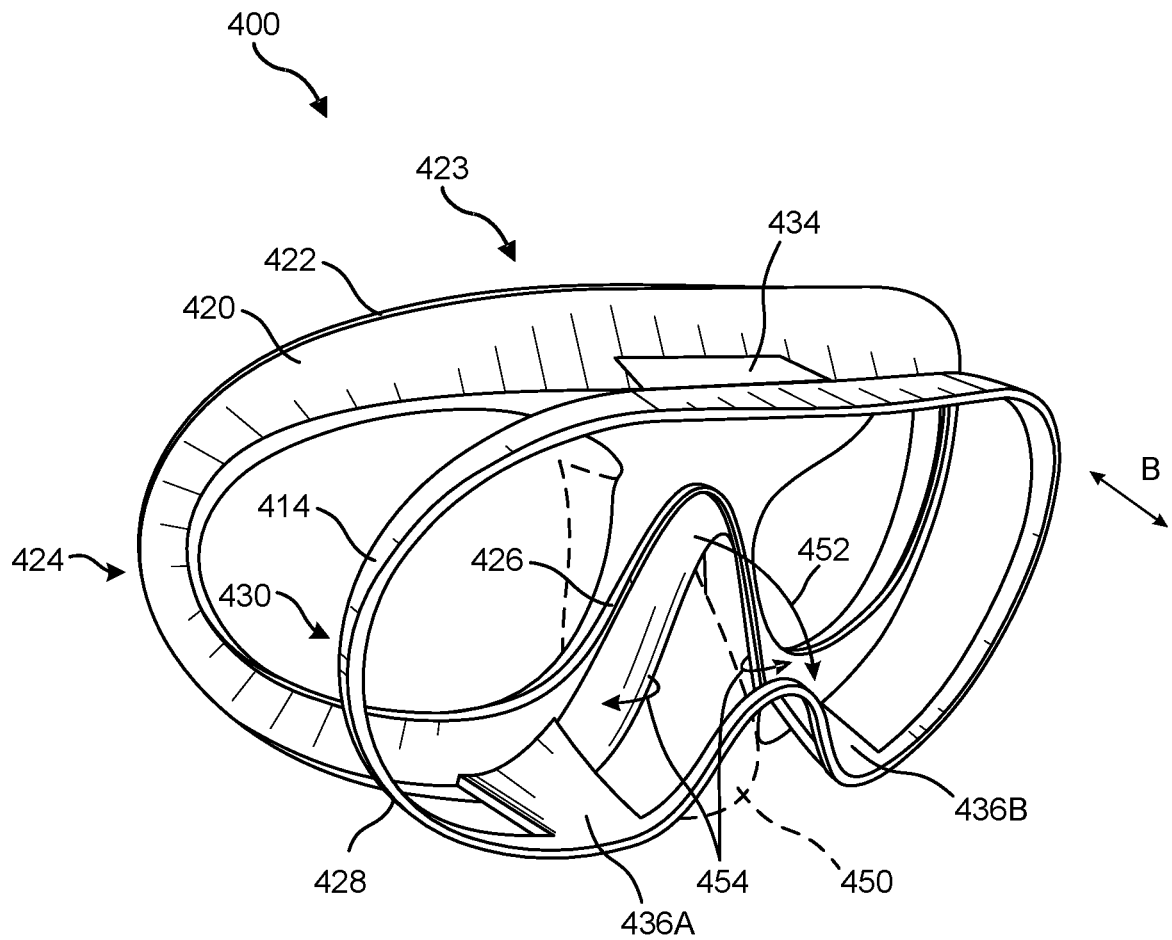
FIG. 4 is a perspective view of a frame body of a facial interface assembly as worn by a user, according to at least one embodiment of the present disclosure.

FIG. 4 is a perspective view of a frame body 423 of a facial interface assembly 404 as worn by a user, according to at least one embodiment of the present disclosure. The user's nose 450 is shown in FIG. 4 to illustrate placement of the facial interface assembly 400 on the user's face. The facial interface assembly 404 may be the same or similar to the facial interface assembly 104 described above with reference to FIGS. 1-3. For example, the facial interface assembly 504 may include a rigid support frame element 414 and a flexible facial interface frame element 420. A facial interface padding 422 may be disposed on an inner (e.g., toward the user's face when worn) surface of the flexible facial interface frame element 420. An outer periphery 424 of the flexible facial interface frame element 420 may be decoupled (e.g., independently movable, lacking a support element) from an outer periphery 430 of the rigid support frame element 414. A nasal bridge portion 426 of the flexible facial interface frame element 420 may be positioned to be over a nasal bridge of the user's nose 450 when worn. As discussed above, the rigid support frame element 414 may be or include a lip 428 with a sufficient width in a forward and backward direction B (relative to the user) to inhibit flexing of the rigid support frame element 414 in the forward and backward direction B. An upper central support element 434 may couple upper portions of the rigid support frame element 414 and flexible facial interface frame element 420 to each other. First and second lower central support elements 436A, 436B may couple lower portions of the rigid support frame element 414 and flexible facial interface frame element 420 to each other.

As shown in FIG. 4, the nasal bridge portion 426 of the flexible facial interface frame element 420 may be configured to flex to conform to the user's nose 450. Different users may have different nose shapes and sizes. The flexing of the nasal bridge portion 426 may accommodate such different nose shapes and sizes for a comfortable fit on a variety of different users. For example, the nasal bridge portion 426 may be configured to flex forward and backward to accommodate user noses 450 with respectively protruding or flat nasal bridges, as indicated by the arrow 452. The nasal bridge portion 426 of the flexible facial interface frame element 420 may, in some embodiments, also be configured to flex inward and outward to accommodate respectively narrow or wide user noses 450, as indicated by the arrows 454. Such movement of the nasal bridge portion 426 may be substantially independent from the rigid support frame element 414. Thus, movement of the nasal bridge portion 426 to conform to a user's facial features (e.g., the user's nose 450) may not result in substantial movement of the rigid support frame element 414.

Figure 5A:
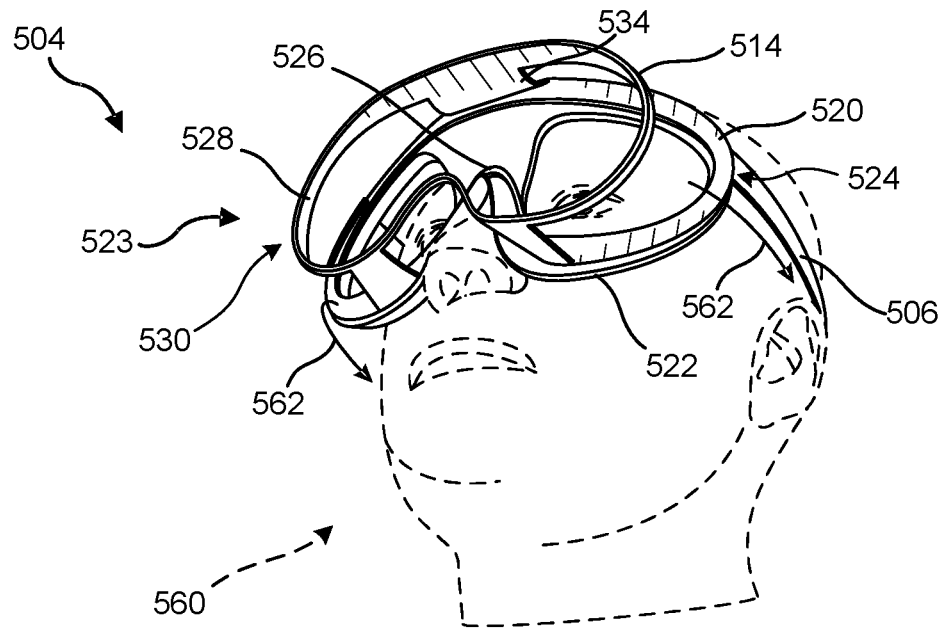
FIG. 5A is a perspective view of a facial interface assembly as worn by a user, according to at least one embodiment of the present disclosure.
Figure 5B:
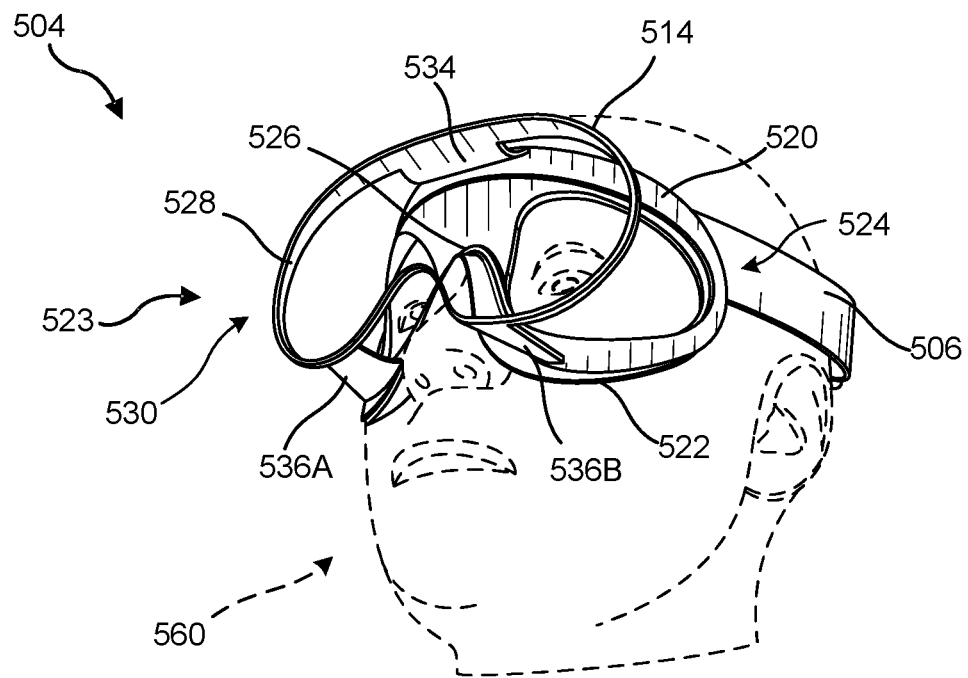
FIG. 5B is a perspective view of the facial interface assembly of FIG. 5A after flexing to conform to the user's facial features.

FIG. 5A is a perspective view of a facial interface assembly 504 as worn by a user, according to at least one embodiment of the present disclosure. FIG. 5B is a perspective view of the facial interface assembly 504 after flexing to conform to a user's head 160. The facial interface assembly 504 may be the same or similar to the facial interface assembly 104 described above with reference to FIGS. 1-3. For example, the facial interface assembly 504 may include a rigid support frame element 514 and a flexible facial interface frame element 520. A head strap 506 may extend backward (relative to the user when the facial interface assembly 504 is worn by the user) from the facial interface assembly 504A to secure the facial interface assembly 504 on the user's head 560. A facial interface padding 522 may be disposed on an inner (e.g., toward the user's head 560 when worn) surface of the flexible facial interface frame element 520. The flexible facial interface frame element 520 may include a nasal bridge portion 526 positioned over the user's nose. The rigid support frame element 514 and the flexible facial interface frame element 520 may be parts of a frame body 523.

As shown in FIGS. 5A and 5B, an outer periphery 524 of the flexible facial interface frame element 520 may be decoupled (e.g., independently movable, lacking a support element) from an outer periphery 530 of the rigid support frame element 514. As discussed above, the rigid support frame element 514 may be or include a lip 528 with a sufficient width in a forward and backward direction (relative to the user) to inhibit flexing of the rigid support frame element 514 in the forward and backward direction. An upper central support element 534 may couple upper portions of the rigid support frame element 514 and flexible facial interface frame element 520 to each other. First and second lower central support elements 536A, 536B may couple lower portions of the rigid support frame element 514 and flexible facial interface frame element 520 to each other. However, the facial interface assembly 504 may lack any support elements between the outer periphery 524 of the flexible facial interface frame element 520 and outer periphery 530 of the of the rigid support frame element 514. Thus, when the facial interface assembly 504 is placed on the user's head 560 and the head strap 506 is tightened, the flexible facial interface frame element 520 may flex backward to conform to the user's head 560, as indicated in FIG. 5A by arrow 562. The facial interface assembly 504 may be conformable to comfortably fit on a variety of different user heads 560 that have different shapes and sizes. The flexibility of the outer periphery 524 of the flexible facial interface frame element 520 may be substantially unimpeded by the rigid support frame element 514.

Figure 6:
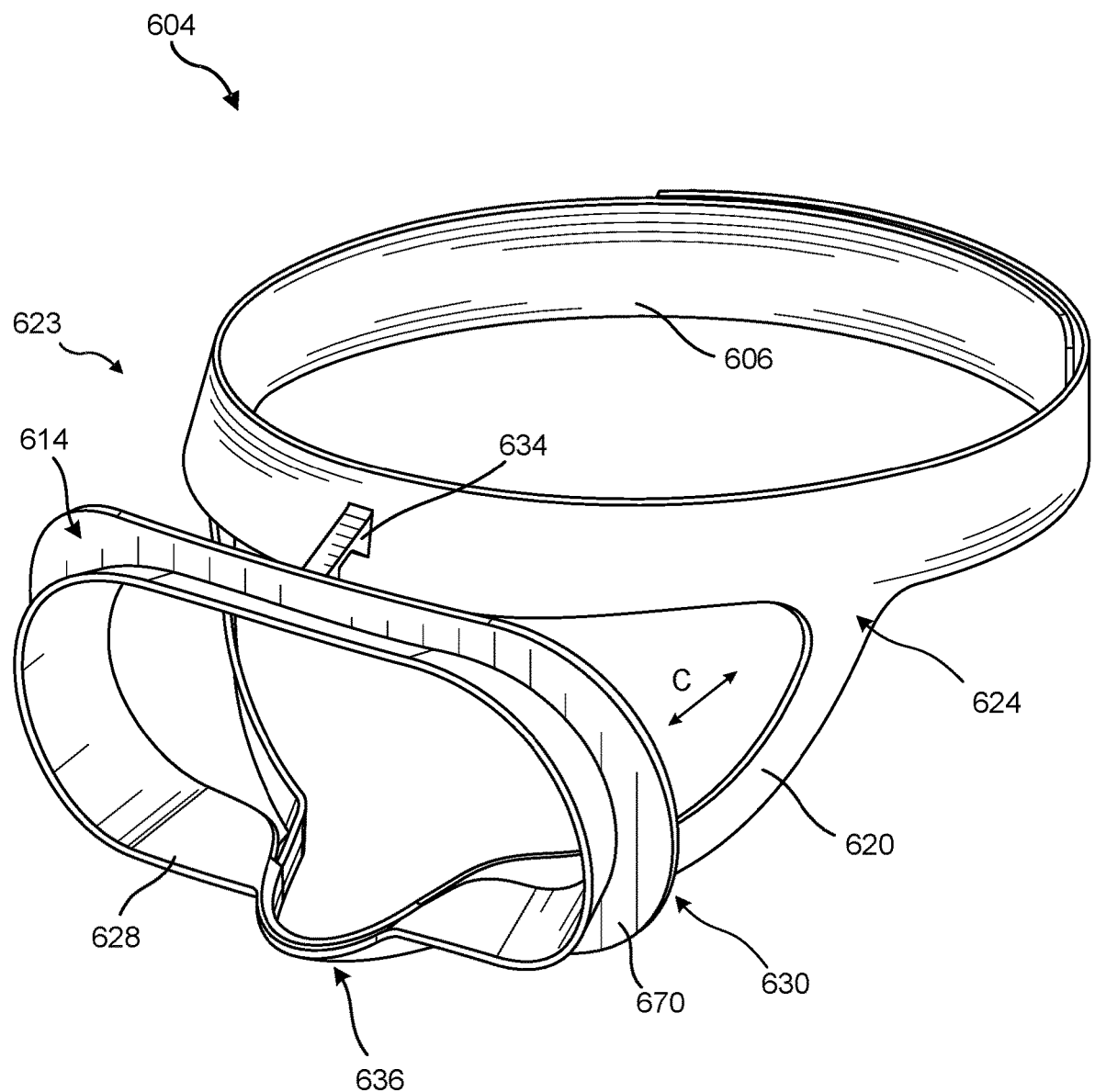
FIG. 6 is a perspective view of a facial interface assembly, according to at least one embodiment of the present disclosure.

FIG. 6 is a perspective view of a facial interface assembly 604 for an HMD system according to at least one additional embodiment. The facial interface assembly 604 may be similar in some respects to the facial interface assembly 104 discussed above. For example, the facial interface assembly 604 may include a rigid support frame element 614 for supporting a display and a flexible facial interface frame element 620 configured to flex to conform to a user's facial features when the facial interface assembly 604 is worn by the user. An outer periphery 624 of the flexible facial interface frame element 620 may be independently movable (e.g., in a forward and backward direction C relative to the user) relative to an outer periphery 630 of the rigid support frame element 614. The rigid support frame element 614 may include a lip 628 having a width in the forward and backward direction C that is sufficient to inhibit flexing of the rigid support frame element 614 in the forward and backward direction C.

As shown in FIG. 6, in some embodiments, the facial interface assembly 604 may also include a head strap 606 that may be an integral portion of the flexible facial interface frame element 620, rather than a separate piece that is coupled to the facial interface assembly 604. The rigid support frame element 614 may include a flange 670 extending outward from a rear portion of the lip 628. The flange 670 may, for example, provide material for connecting other components of the facial interface assembly 604 or a corresponding HMD system. The flange 670 may also increase a rigidity of the rigid support frame element 614.

The facial interface assembly 604 may include a single upper central support element 634 coupled to and extending between an upper portion of the rigid support frame element 614 and an upper portion of the flexible facial interface frame element 620. The upper central support element 634 may be positioned to be over (e.g., above) the user's nose when the facial interface assembly is worn by the user. The facial interface assembly 604 may also include a single lower support element 636 coupling the rigid support frame element 614 to the flexible facial interface frame element 620. The lower support element 636 may be positioned to be over (e.g., on) the user's nose when the facial interface assembly 604 is worn by the user. In some examples, the lower support element 636 may be an extension (e.g., protrusion) of the flexible facial interface frame element 620, and the lower support element 636 may be coupled (e.g., attached, adhered, welded, integrally formed, fastened, etc.) to the rigid support frame element 614. In additional examples, the lower support element 636 may be a separate element positioned between the flexible facial interface frame element 620 and the rigid support frame element 614. As shown in FIG. 6, the outer periphery 624 of the flexible facial interface frame element 620 may be independently movable relative to the outer periphery 630 of the rigid support frame element 614. For example, the facial interface assembly 604 may lack a support element positioned between these outer peripheries 624, 630.

The rigid support frame element 614, flexible facial interface frame element 620, upper central support element 634, and lower support element 636 may be parts of a frame body 623. In some examples, the head strap 606 may also be a part of the frame body 623. In some embodiments, the components of the frame body 623 may be integrally formed (e.g., via molding, three-dimensional printing, etc.) to define an integral, unitary frame body 623.

Figure 7:
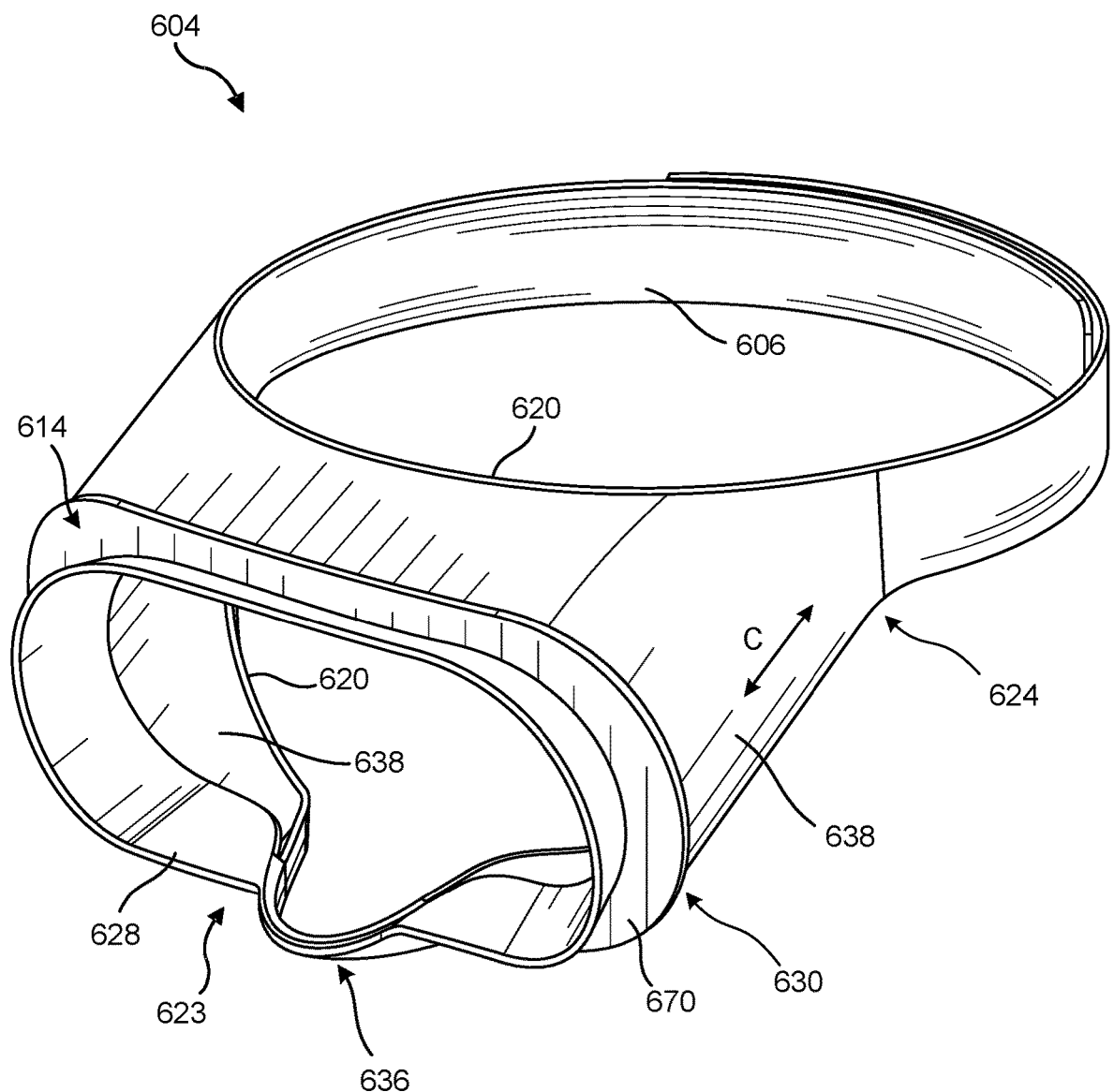
FIG. 7 is a perspective view of a facial interface assembly, according to at least one embodiment of the present disclosure.

FIG. 7 is a perspective view of the facial interface assembly 604 with an extensible material 638 positioned between the rigid support frame element 614 and the flexible facial interface frame element 620, according to at least one embodiment of the present disclosure. By way of example and not limitation, the extensible material 638 may be a flexible foam material, such as an open cell foam material or a closed cell foam material. In one example, the extensible material 638 may be a polyurethane foam material. The extensible material 638 may be formed by, for example, positioning the frame body 623 in a mold cavity and overmolding the frame body 623 with a foam material. Alternatively, the extensible material 638 may be preformed and coupled (e.g., adhered, bolted, clipped, engaged, etc.) to the frame body 623.

Figure 8:
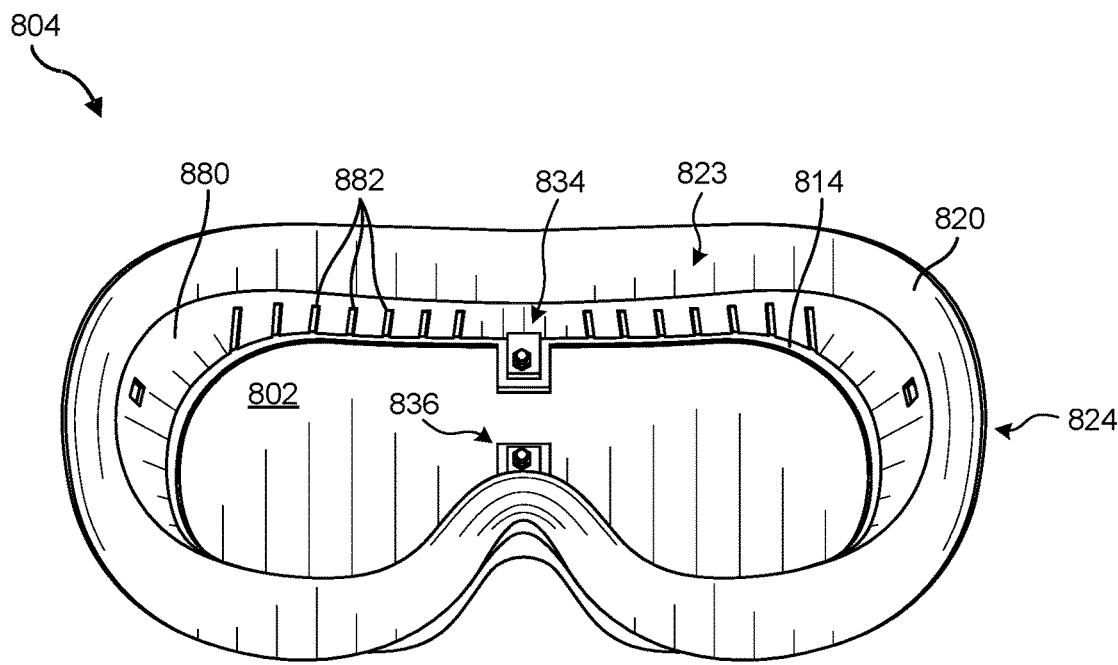
FIG. 8 is a back perspective view of a facial interface assembly, according to at least one embodiment of the present disclosure.
Figure 9:
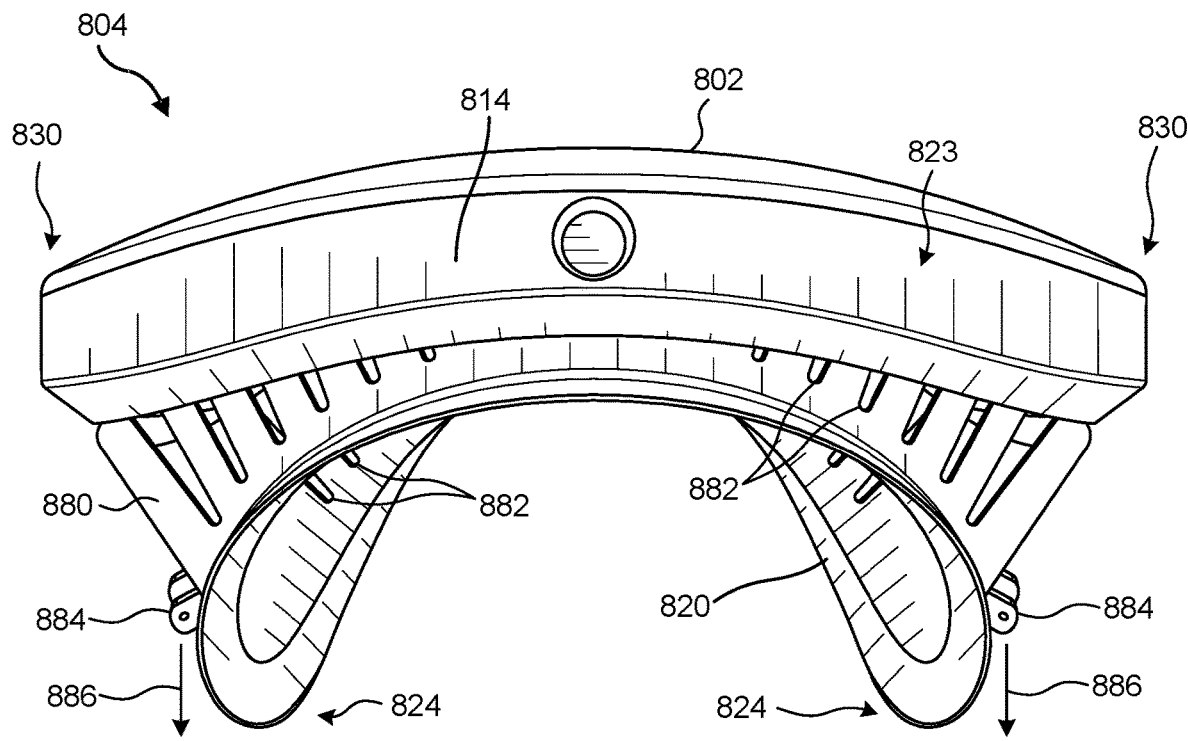
FIG. 9 is a top perspective view of the facial interface assembly of FIG. 8, shown with a flexible facial interface frame element thereof in a flexed position, according to at least one embodiment of the present disclosure.

FIG. 8 is a back perspective view of a facial interface assembly 804 for an HMD system according to additional embodiments. FIG. 9 is a top perspective view of the facial interface assembly 804, showing a flexible facial interface frame element 820 thereof in a flexed position. A frame body 823 of the facial interface assembly 804 may include the flexible facial interface frame element 820 and a rigid support frame element 814 for supporting a display 802. The flexible facial interface frame element 820 and the rigid support frame element 814 may be coupled to each other with an upper central support element 834 and a lower central support element 836. For example, the central support elements 834, 836 may include screws or other fasteners.

The flexible facial interface frame element 820 may include a flexible flange 880 extending forward (relative to a user wearing the facial interface assembly 804) toward the rigid support frame element 814. The flexible flange 880 may be formed with slits 882 to increase a flexibility of the flexible flange 880 and of the flexible facial interface frame element 820, as shown in FIGS. 8 and 9. Additionally, the slits 882 may improve a breathability of the facial interface assembly 804. The flexible flange 880 may be present to provide a standoff between the flexible facial interface frame element 820 and the rigid support frame element 814 and to block at least some external visible light from reaching the user's eyes.

The flexible facial interface frame element 820 may also include head strap attachment features 884 (FIG. 9) at or near an outer periphery 824 thereof. The outer periphery 824 of the flexible facial interface frame element 820 may be independently movable in the forward and backward direction (relative to a user wearing the facial interface assembly 804) relative to an outer periphery 830 of the rigid support frame element 814. For example, as illustrated in FIG. 9, tightening a head strap may pull the head strap attachment features 884 and the outer periphery 824 of the flexible facial interface frame element 820 in a direction away from the rigid support frame element 814, as shown by arrows 886. Upon flexing of the flexible facial interface frame element 820 backwards, the slits 882 may widen to allow the flexible flange 880 to stretch and the flexible facial interface frame element 820 to conform to the user's facial features (e.g., head). In some embodiments, an extensible material (e.g., an extensible fabric and/or an extensible foam) may be positioned over an exterior of the flexible flange 880 and between the rigid support frame element 814 and the flexible facial interface frame element 820, as explained above.

Figure 10:
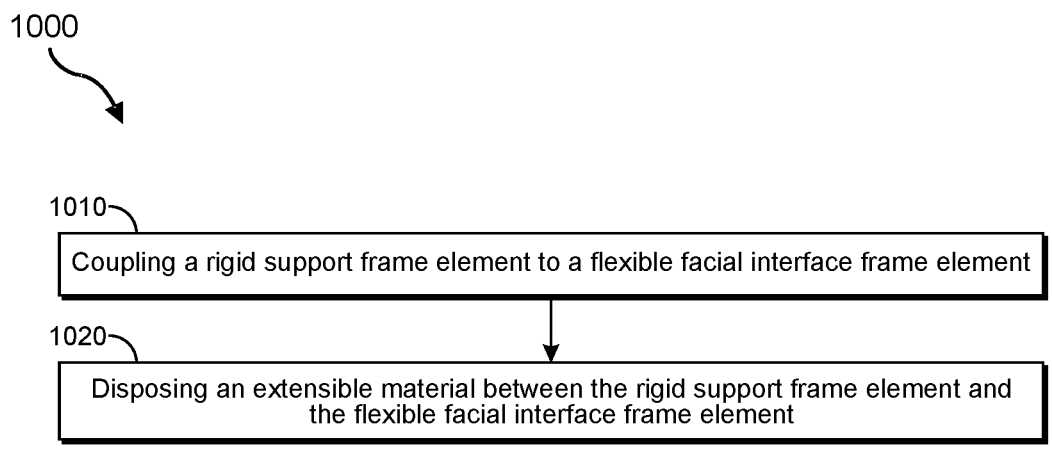
FIG. 10 is a flow diagram illustrating a method of forming a facial interface assembly, according to at least one embodiment of the present disclosure.

FIG. 10 is a flow diagram illustrating a method 1000 of forming a facial interface assembly, according to at least one embodiment of the present disclosure. At operation 1010, a rigid support frame element may be coupled to a flexible facial interface frame element. Operation 1010 may be performed in a variety of different ways. For example, coupling the rigid support frame element to the flexible facial interface frame element may include forming these frame elements as an integral, unitary frame body, such as by molding or three-dimensional printing. Alternatively, the rigid support frame element and the flexible facial interface frame element may be formed separately and coupled to each other. In some embodiments, at least one central support element (e.g., an upper central support element and at least one lower central support element) may be used to couple the rigid support frame element and the flexible facial interface frame element to each other, as described above. The coupling of these two frame elements to each other may include coupling a central portion thereof to each other, while leaving outer peripheries of the rigid support frame element and of the flexible facial interface frame element decoupled (e.g., not connected by any rigid or otherwise non-extensible support element) from each other. Decoupling the outer peripheries may enable substantially independent movement of the outer periphery of the flexible facial interface frame element relative to the rigid support frame element in the forward and backward direction (relative to a user wearing the facial interface assembly), as described above.

At operation 1020, an extensible material may be disposed between the rigid support frame element and the flexible facial interface frame element. The extensible material may be configured to extend upon flexing of the flexible facial interface frame element away from the rigid support frame element and to retract upon flexing of the flexible facial interface frame element toward the rigid support frame element, such as to conform to facial features of a user. Operation 820 may be performed in a variety of different ways. For example, a flexible fabric (e.g., a woven fabric material, a non-woven fabric material, a fabric material that is at least partially transmissive to visible light, a fabric material that is opaque to visible light, etc.) may be disposed between the rigid support frame element and the flexible facial interface frame element. Additionally or alternatively, a flexible foam material (e.g., a closed cell foam material, an open cell foam material, a polyurethane foam material, etc.) may be disposed between the rigid support frame element and the flexible facial interface frame element.

In some examples, the method 1000 of forming the facial interface assembly may include additional operations, such as coupling a head strap to the flexible facial interface frame element, disposing a facial interface padding (e.g., foam) material on an inner surface of the flexible facial interface frame element, removably coupling a display (e.g., an artificial reality display) to the rigid support frame element, coupling an electrical cable to the rigid support frame element, etc.

Accordingly, disclosed are facial interface assemblies and related systems and methods that may be useful for, by way of example and not limitation, HMD systems (e.g., artificial reality systems). The facial interface assemblies may include a rigid support frame element for supporting a display and a flexible facial interface assembly. At least outer peripheries of the flexible facial interface assemblies may be independently movable in forward and backward directions relative to the rigid support frame element, resulting in a versatile, adaptable, and comfortable fit on a user's face.

Embodiments of the instant disclosure may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

The preceding description has been provided to enable others skilled in the art to best utilize various aspects of the example embodiments disclosed herein. This example description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A facial interface assembly for a head-mounted display system, comprising:
   a rigid support frame element dimensioned to physically support a display of a head-mounted display system; and
   a flexible facial interface frame element configured to rest against a user's face laterally outside of the user's eyes and to flex to conform to the user's facial features when the facial interface assembly is worn by the user, the flexible facial interface frame element comprising at least one central support element that structurally supports the flexible facial interface frame element in a laterally central region of the flexible facial interface frame element,
   wherein a laterally outer peripheral region of the flexible facial interface frame element laterally outside of the at least one central support element lacks any support element between the laterally outer peripheral region of the flexible facial interface frame element and a laterally outer peripheral region of the rigid support frame element such that the laterally outer peripheral region of the flexible facial interface frame element is independently movable relative to the rigid support frame element.

2. The facial interface assembly of claim 1, further comprising an extensible material disposed between the rigid support frame element and the flexible facial interface frame element and configured to extend upon flexing of the flexible facial interface frame element away from the rigid support frame element and to retract upon flexing of the flexible facial interface frame element toward the rigid support frame element.

3. The facial interface assembly of claim 2, wherein the extensible material comprises a flexible fabric material.

4. The facial interface assembly of claim 3, wherein the flexible fabric material comprises at least one of:
   a woven fabric material;
   a non-woven fabric material;
   a fabric material that is at least partially transmissive to visible light; or
   a fabric material that is opaque to visible light.

5. The facial interface assembly of claim 2, wherein the extensible material comprises a flexible foam material.

6. The facial interface assembly of claim 5, wherein the flexible foam material comprises at least one of:
   a closed cell foam material; or
   an open cell foam material.

7. The facial interface assembly of claim 1, wherein the at least one central support element comprises multiple central support elements.

8. The facial interface assembly of claim 1, wherein the at least one central support element comprises an upper central support element coupling an upper portion of the rigid support frame element to an upper portion of the flexible facial interface frame element, wherein the upper central support element is positioned to be over the user's nose when the facial interface assembly is worn by the user.

9. The facial interface assembly of claim 8, wherein the at least one central support element further comprises at least one lower central support element coupling a lower portion of the rigid support frame element to a lower portion of the flexible facial interface frame element.

10. The facial interface assembly of claim 9, wherein the at least one lower central support element comprises a single lower central support element positioned to be over the user's nose when the facial interface assembly is worn by the user.

11. The facial interface assembly of claim 9, wherein the at least one lower central support element comprises a first lower central support element positioned to be under the user's first eye and a second lower central support element positioned to be under the user's second eye when the facial interface assembly is worn by the user.

12. The facial interface assembly of claim 11, wherein the flexible facial interface frame element comprises a nasal bridge portion that is configured to flex inward or outward to accommodate a shape of the user's nasal bridge when the facial interface assembly is worn by the user.

13. The facial interface assembly of claim 1, wherein the rigid support frame element and the flexible facial interface frame element comprise a same material.

14. The facial interface assembly of claim 13, wherein the rigid support frame element and the flexible facial interface frame element are parts of a unitary, integral frame body.

15. The facial interface assembly of claim 1, further comprising a head strap extending from the laterally outer peripheral region of the flexible facial interface frame element, such that the laterally outer peripheral region of the flexible facial interface frame element flexes away from the rigid support element when the head strap is tightened around a head of the user, wherein the head strap comprises a same material as the flexible facial interface frame element.

16. The facial interface assembly of claim 1, wherein the flexible facial interface frame element comprises a flexible flange that includes slits to increase a flexibility of the flexible facial interface frame element.

17. A head-mounted display system, comprising:
   a display configured to display images to a user's eyes when the head-mounted display system is worn by the user; and
   a facial interface assembly, comprising:
     a rigid support frame element configured to physically support the display in front of the user's eyes when the facial interface assembly is worn by the user;
     a flexible facial interface frame element configured to rest against the user's face laterally outside of the user's eyes when the head-mounted display system is worn by the user; and
     at least one central support element that structurally supports the flexible facial interface frame element in a laterally central region of the flexible facial interface frame element, wherein a laterally outer peripheral region of the flexible facial interface frame element laterally outside of the at least one central support element lacks any support element between the laterally outer peripheral region of the flexible facial interface frame element and the rigid support frame element such that the laterally outer peripheral region of the flexible facial interface frame element is independently movable relative to the rigid support frame element.

18. The head-mounted display system of claim 17, wherein the display is removable and replaceable relative to the facial interface assembly.

19. The head-mounted display system of claim 17, wherein the facial interface assembly further comprises an extensible material disposed between the rigid support frame element and the flexible facial interface frame element and configured to extend upon flexing of the flexible facial interface frame element away from the rigid support frame element.

20. A method of forming a facial interface assembly for a head-mounted display system, the method comprising:

coupling a laterally central region of a flexible facial interface frame element to a rigid support frame element with at least one central support element, wherein the rigid support element is configured to physically support a display of a head-mounted display system, the flexible facial interface frame element is configured to rest against a user's face laterally outside of the user's eyes, and a laterally outer peripheral region of the flexible facial interface frame element laterally outside of the at least one central support element lacks any support element and is structurally decoupled from and independently movable relative to a laterally outer peripheral region of the rigid support frame element; and disposing an extensible material between the rigid support frame element and the flexible facial interface frame element, wherein the extensible material is configured to extend upon flexing of the flexible facial interface frame element away from the rigid support frame element and to retract upon flexing of the flexible facial interface frame element toward the rigid support frame element.

\* \* \* \* \*